United States Patent
Oya et al.

(10) Patent No.: US 9,795,566 B2
(45) Date of Patent: Oct. 24, 2017

(54) IMIDAZOLE COMPOUND AND LIPOSOME CONTAINING SAME

(71) Applicant: FUJIFILM Corporation, Tokyo (JP)

(72) Inventors: Toyohisa Oya, Ashigarakami-gun (JP); Ayumi Ishiyama, Ashigarakami-gun (JP); Naoyuki Nishikawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/406,050

(22) Filed: Jan. 13, 2017

(65) Prior Publication Data

US 2017/0119667 A1 May 4, 2017

Related U.S. Application Data

(63) Continuation of application No. PCT/JP2015/070399, filed on Jul. 16, 2015.

(30) Foreign Application Priority Data

Jul. 17, 2014 (JP) ................................. 2014-146810

(51) Int. Cl.
- *A61K 9/127* (2006.01)
- *A61K 47/22* (2006.01)
- *C07D 233/64* (2006.01)

(52) U.S. Cl.
CPC ............ *A61K 9/1272* (2013.01); *A61K 47/22* (2013.01); *C07D 233/64* (2013.01)

(58) Field of Classification Search
None
See application file for complete search history.

(56) References Cited

U.S. PATENT DOCUMENTS

| | | | |
|---|---|---|---|
| 6,093,816 | A | 7/2000 | Lin et al. |
| 2005/0164963 | A1 | 7/2005 | Essler et al. |
| 2006/0171956 | A1 | 8/2006 | Bareholz et al. |
| 2012/0064148 | A1 | 3/2012 | Takeoka et al. |
| 2014/0200257 | A1 | 7/2014 | Rajeev et al. |

FOREIGN PATENT DOCUMENTS

| | | |
|---|---|---|
| JP | 2005-517739 A | 6/2005 |
| JP | 2005-526727 A | 9/2005 |
| JP | 2006-527761 A | 12/2006 |
| JP | 2014-505145 A | 2/2014 |
| WO | 2006/118327 A1 | 11/2006 |
| WO | 2010/104128 A1 | 9/2010 |

OTHER PUBLICATIONS

International Search Report for PCT/JP2015/070399 dated Sep. 29, 2015 [PCT/ISA/210.
Written Opinion for PCT/JP2015/070399 dated Sep. 29, 2015 [PCT/ISA/237.
International Preliminary Report on Patentability with translation of Written Opinion issued from the International Bureau in counterpart International Application No. PCT/JP2015/070399 dated Jan. 26, 2017.
Office Action in Japanese Patent Application No. 2014-146810 dated Sep. 5, 2017.

*Primary Examiner* — Alicia L Otton
(74) *Attorney, Agent, or Firm* — Sughrue Mion, PLLC

(57) ABSTRACT

Provided are a novel imidazole compound which has a high stability of the compound itself; and a novel imidazole compound which is useful as a membrane-constituting lipid of liposomes. Disclosed are a compound represented by the following General Formula (1), and a liposome containing the same compound.

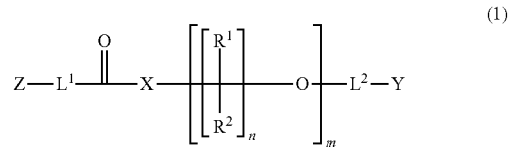

In the formula, Z is an imidazolyl group which may be substituted, $L^1$ is an alkylene group having 1 to 4 carbon atoms which may be substituted, X is an oxygen atom or a nitrogen-containing substituent, n is an integer of 2 to 4, m is an integer of 1 to 20, $L^2$ is a divalent linking group having 1 to 6 carbon atoms, Y is a nitrogen-containing group, $R^1$ and $R^2$ are a hydrogen group or an alkyl group having 1 to 6 carbon atoms, $R^3$ is a hydrogen atom or a substituent, and $R^4$ and $R^5$ are an alkyl group having 1 to 40 carbon atoms.

4 Claims, 2 Drawing Sheets

SEQUENCE LISTING

```
<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 1
guucagacca cuucagcuu                                                 19

<210> SEQ ID NO 2
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 2
caagucuggu gaagucgaa                                                 19
```

IMIDAZOLE COMPOUND AND LIPOSOME CONTAINING SAME

CROSS-REFERENCE TO RELATED APPLICATIONS

The present application is a continuation of PCT/JP2015/070399 filed on Jul. 16, 2015 and claims priority under 35 U.S.C. §119 of Japanese Patent Application No. 146810/2014 filed on Jul. 17, 2014.

BACKGROUND OF THE INVENTION

1. Field of the Invention

The present invention relates to a novel imidazole compound, preferably an imidazole compound useful as a membrane-constituting lipid of a liposome, and a liposome containing the same.

2. Description of the Related Art

Recently, studies have been made for liposomes by which intraliposomal encapsulation of useful substances or release of useful substances in target cells can be controlled in response to an external pH. In particular, in a carrier which delivers a charged active ingredient such as nucleic acid, use of a pH-responsive lipid having pH-dependent charge characteristics as a membrane-constituting lipid of liposomes has been studied (JP2005-517739A).

To date, compounds containing an imidazole moiety (JP2005-526727A and U.S. Pat. No. 6,093,816A), and compounds containing a histidine moiety and a glutamic acid dialkyl ester moiety (WO2006/118327A) have been disclosed as pH-responsive lipids.

SUMMARY OF THE INVENTION

However, in a known imidazole compound or a compound containing a histidine moiety and a glutamic acid dialkyl ester moiety each of which functioning as a pH-responsive lipid, there is a problem associated with stability of the compound itself. For example, it has not been sufficient to use such a compound as a membrane-constituting lipid of liposomes.

An object of the present invention is to provide a novel imidazole compound which has a high stability of the compound itself. Another object of the present invention is to provide a novel imidazole compound which has a high stability of the compound itself and is useful as a membrane-constituting lipid of liposomes.

As a result of intensive studies to solve the foregoing problems, the present inventors have discovered a novel imidazole compound having a specific dialkylamino group at the molecular end thereof and also having a specific repeating structure in the molecule. The present invention has been completed based on such a discovery.

That is, the means for solving the problems are as follows.

[1] A compound represented by the following General Formula (1):

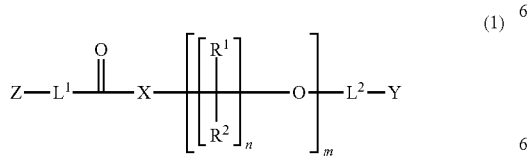

in Formula (1),
Z is an imidazolyl group which may have a substituent,
$L^1$ is an alkylene group having 1 to 4 carbon atoms which may have a substituent, and
X is an oxygen atom or a group represented by the following Formula (2),

* is a position of bonding,
n is an integer of 2 to 4,
m is an integer of 1 to 20,
$L^2$ is a divalent linking group having 1 to 6 carbon atoms, and
Y is a group represented by the following Formula (3),

$R^1$ and $R^2$ are the same or different and are a hydrogen atom or an alkyl group having 1 to 6 carbon atoms,
$R^3$ is a hydrogen atom or a substituent, and
$R^4$ and $R^5$ are the same or different and are an alkyl group having 1 to 40 carbon atoms.

[2] The compound according to [1], in which $L^1$ is an alkylene group represented by the following Formula (4):

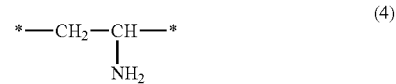

in the formula, * represents a position of bonding.

[3] A liposome comprising the compound according to [1] or [2].

According to the present invention, it is possible to provide a novel imidazole compound. Further, according to the present invention, it is possible to provide a novel imidazole compound which has a high stability of the compound itself and is useful as a membrane-constituting lipid of liposomes.

DESCRIPTION OF THE PREFERRED EMBODIMENTS

Figure 1:
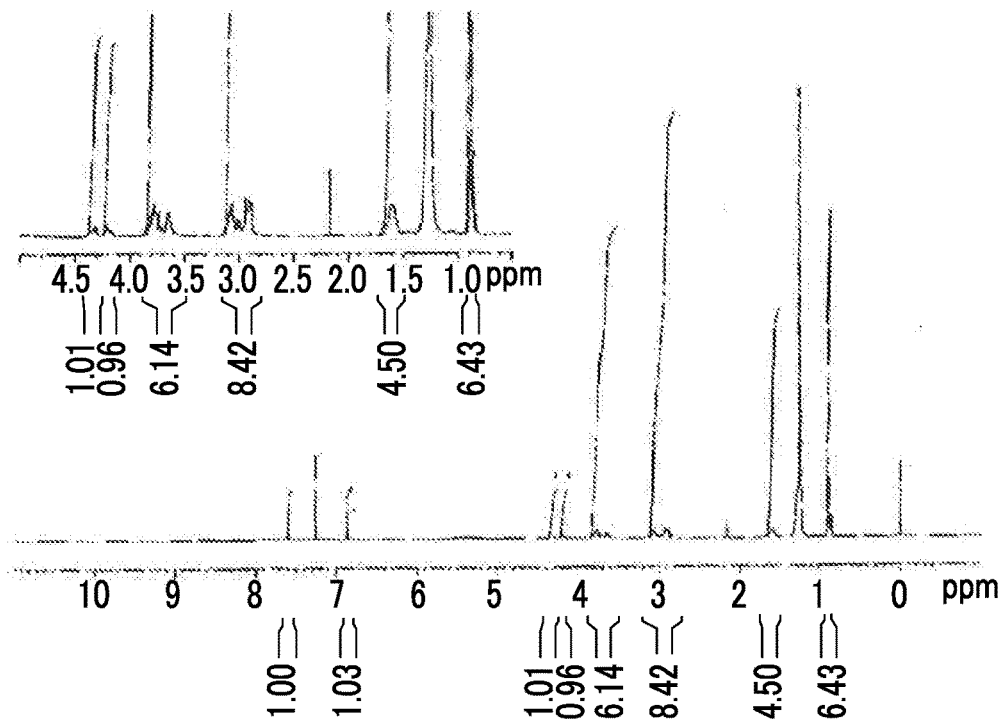
FIG. 1 is a $^1$H-NMR spectrum of Compound I-7 in Example 1.
Figure 2:
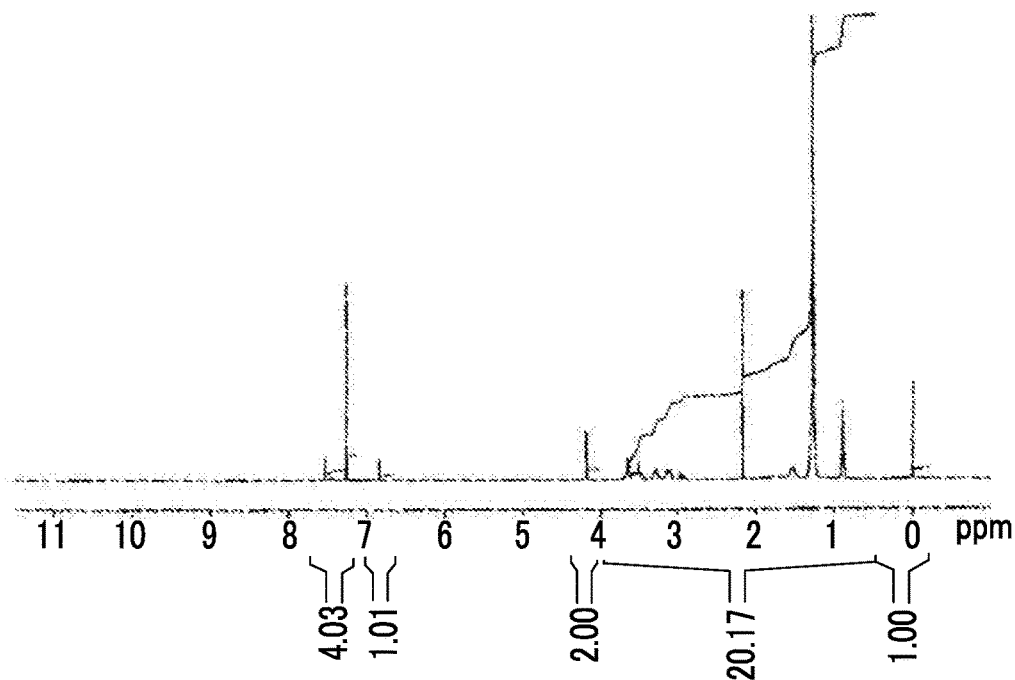
FIG. 2 is a $^1$H-NMR spectrum of Compound I-88 in Example 2.
Figure 3:
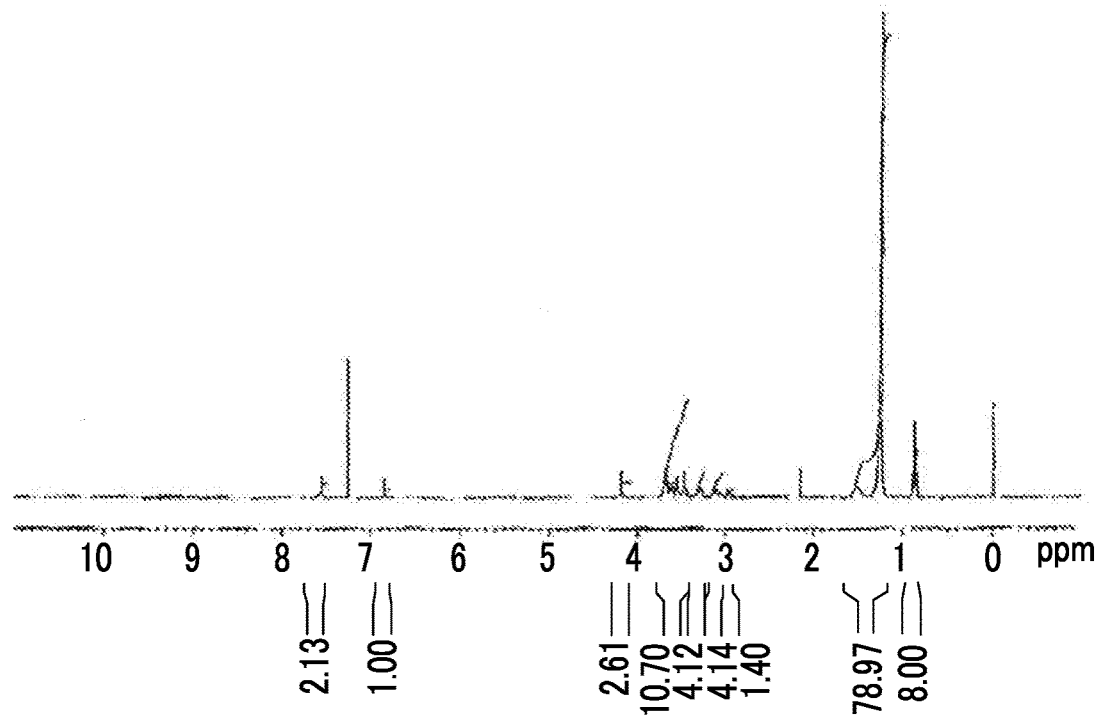
FIG. 3 is a $^1$H-NMR spectrum of Compound I-90 in Example 3.

Hereinafter, the present invention will be described in detail.

The numerical value ranges shown with "to" in the present specification means ranges including the numerical values indicated before and after "to" as the minimum and maximum values, respectively.

In the present specification, unless otherwise specified, the substituent refers to Substituent Group A given below. Substituents mentioned in Substituent Group A may further have a substituent.

Substituent Group A: a halogen atom, an alkyl group having 1 to 30 carbon atoms, a cycloalkyl group having 3 to 30 carbon atoms, a bicycloalkyl group having 5 to 30 carbon atoms, an alkenyl group having 2 to 30 carbon atoms, a cycloalkenyl group having 3 to 30 carbon atoms, a bicycloalkenyl group having 5 to 30 carbon atoms, an alkynyl group having 2 to 30 carbon atoms, an aryl group, a heterocyclic group, a cyano group, a hydroxyl group, a nitro group, a carboxyl group, an alkoxy group having 1 to 30 carbon atoms, an aryloxy group, a silyloxy group, a heterocyclic oxy group, an acyloxy group, a carbamoyloxy group, an alkoxycarbonyloxy group having 2 to 30 carbon atoms, an aryloxycarbonyloxy group, an amino group, an acylamino group, an aminocarbonylamino group, an alkoxycarbonylamino group, an aryloxycarbonylamino group, a sulfamoylamino group, an alkylsulfonylamino group having 1 to 30 carbon atoms, an arylsulfonylamino group, a mercapto group, an alkylthio group having 1 to 30 carbon atoms, an arylthio group, a heterocyclic thio group, a sulfamoyl group, a sulfo group, an alkylsulfinyl group having 1 to 30 carbon atoms, an arylsulfinyl group, an alkylsulfonyl group having 1 to 30 carbon atoms, an arylsulfonyl group, an acyl group, an aryloxycarbonyl group, a benzyloxycarbonyl group, a 9-fluorenylmethyloxycarbonyl group, an alkoxycarbonyl group having 1 to 30 carbon atoms, a carbamoyl group, an arylazo group, a heterocyclic azo group, an imido group, a phosphino group, a phosphinyl group, a phosphinyloxy group, a phosphinylamino group, a silyl group, and an oxo group.

Examples of the halogen atom include a fluorine atom, a chlorine atom, a bromine atom and an iodine atom.

The alkyl group having 1 to 30 carbon atoms may be linear or branched, and examples thereof include a methyl group, an ethyl group, an n-propyl group, an isopropyl group, and a t-butyl group.

Examples of the cycloalkyl group having 3 to 30 carbon atoms include a cyclohexyl group, a cyclopentyl group, and a 4-n-dodecylcyclohexyl group.

The bicycloalkyl group having 5 to 30 carbon atoms may be, for example, a bicyclo[1,2,2]heptan-2-yl group.

The alkenyl group having 2 to 30 carbon atoms may be linear or branched, and examples thereof include a vinyl group, an allyl group, and a prenyl group.

Examples of the cycloalkenyl group having 3 to 30 carbon atoms include a 2-cyclopenten-1-yl group and a 2-cyclohexen-1-yl group.

The bicycloalkenyl group having 5 to 30 carbon atoms may be, for example, a bicyclo [1,2,2]hept-2-en-1-yl group.

Examples of the alkynyl group having 2 to 30 carbon atoms include an ethynyl group and a propargyl group.

Examples of the aryl group include a phenyl group and a naphthyl group.

Examples of the heterocyclic group include a 2-furanyl group, a 2-thienyl group, a 2-pyrimidinyl group, and a 2-benzothiazolinyl group.

Examples of the alkoxy group having 1 to 30 carbon atoms include a methoxy group, an ethoxy group, and an isopropoxy group.

Examples of the aryloxy group may be, for example, a phenoxy group.

The heterocyclic oxy group may be, for example, a 1-phenyltetrazole-5-oxy group.

Examples of the acyloxy group include a formyloxy group and an acetyloxy group.

Examples of the carbamoyloxy group include an N,N-dimethylcarbamoyloxy group and an N,N-diethylcarbamoyloxy group.

Examples of the alkoxycarbonyloxy group having 2 to 30 carbon atoms include a methoxycarbonyloxy group and an ethoxycarbonyloxy group.

The aryloxycarbonyloxy group may be, for example, a phenoxycarbonyloxy group.

Examples of the acylamino group include a formylamino group and an acetylamino group.

Examples of the aminocarbonylamino group include a methoxycarbonylamino group and an ethoxycarbonylamino group.

The aryloxycarbonylamino group may be, for example, a phenoxycarbonylamino group.

The alkylsulfonylamino group having 1 to 30 carbon atoms may be, for example, a methylsulfonylamino group.

The arylsulfonylamino group may be, for example, a phenylsulfonylamino group.

Examples of the alkylthio group having 1 to 30 carbon atoms include a methylthio group and an ethylthio group.

The arylthio group may be, for example, a phenylthio group.

Examples of the heterocyclic thio group include a 2-benzothiazolylthio group and a 1-phenyltetrazol-5-ylthio group.

Examples of the alkylsulfinyl group having 1 to 30 carbon atoms include a methylsulfinyl group and an ethylsulfinyl group.

The arylsulfinyl group may be, for example, a phenylsulfinyl group.

Examples of the alkylsulfonyl group having 1 to 30 carbon atoms include a methylsulfonyl group and an ethylsulfonyl group.

The arylsulfonyl group may be, for example, a phenylsulfonyl group.

Examples of the acyl group include a formyl group, an acetyl group, and a pivaloyl group.

The aryloxycarbonyl group may be, for example, a phenoxycarbonyl group.

Examples of the alkoxycarbonyl group having 1 to 30 carbon atoms include a methoxycarbonyl group and an ethoxycarbonyl group.

The arylazo group may be, for example, a phenylazo group.

The imidazole compound represented by General Formula (1) (hereinafter, often referred to as compound of the present invention), which is an aspect of the present invention, will be described in detail.

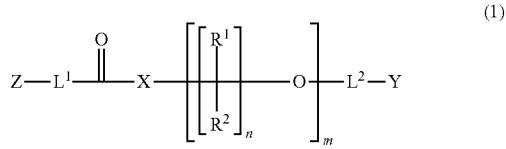

(1)

In General Formula (1), Z is an imidazolyl group which may have a substituent. The position at which the imidazolyl group is bonded to $L^1$ is not particularly limited and may be any of, for example, 1-position, 2-position, 4-position, and 5-position. The position of bonding is preferably 2-position, 4-position, or 5-position, and more preferably 4-position or 5-position.

In a case where the imidazolyl group of Z has a substituent, the substituent is not particularly limited. The substituent is preferably a substituent selected from Substituent Group A, and more preferably a substituent selected from a methyl group, a t-butyl group, an acetyl group, a trifluoroacetyl group, a t-butoxycarbonyl group, a benzyloxycarbonyl group and a 9-fluorenylmethyloxycarbonyl group.

Z is still more preferably an unsubstituted imidazolyl group.

In General Formula (1), $L^1$ is an alkylene group having 1 to 4 carbon atoms which may have a substituent. The number of carbon atoms in the alkylene group of $L^1$ is preferably 2 to 4, more preferably 2 to 3, and still more preferably 2.

In a case where the alkylene group of $L^1$ has a substituent, the substituent is not particularly limited. The substituent is preferably a substituent selected from Substituent Group A, and more preferably an amino group which may have a substituent. Examples of the substituent of the amino group is preferably a substituent selected from Substituent Group A, and more preferably a substituent selected from a t-butoxycarbonyl group, a 9-fluorenylmethyloxycarbonyl group, a 2,2,2-trichloroethoxycarbonyl group, an aryloxycarbonyl group, a benzyloxycarbonyl group, an acetyl group, a trifluoroacetyl group, a phthaloyl group, a 4-toluenesulfonyl group and a 2-nitrobenzenesulfonyl group.

The alkylene group of $L^1$ is particularly preferably a group represented by the following Formula (4).

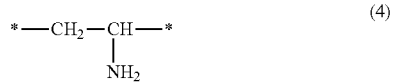

(4)

In the formula, * represents a position of bonding. In the present invention, it is preferred that the bonding position of *—CH< is bonded to the >C=O side of General Formula (1), and the bonding position of *—CH$_2$— is bonded to the Z side of General Formula (1).

In General Formula (1), X is an oxygen atom or a group represented by the following Formula (2).

(2)

In Formula (2), $R^3$ represents a hydrogen atom or a substituent. The substituent is preferably any group substitutable on the nitrogen atom and selected from Substituent Group A, and more preferably a substituent selected from a hydrogen atom, an alkyl group having 1 to 30 carbon atoms, an acetyl group, a trifluoroacetyl group, a t-butoxycarbonyl group, a benzyloxycarbonyl group and a 9-fluorenylmethyloxycarbonyl group.

X is particularly preferably an oxygen atom or a group where $R^3$ in the group represented by Formula (2) is a hydrogen atom.

In General Formula (1), $R^1$ and $R^2$ are the same or different and are a hydrogen atom or an alkyl group having 1 to 6 carbon atoms. Preferred is an alkyl group having 1 to 5 carbon atoms, more preferred is an alkyl group having 1 to 4 carbon atoms, and still more preferred is an alkyl group having 1 to 3 carbon atoms. It is particularly preferred that both of $R^1$ and $R^2$ are a hydrogen atom or one of $R^1$ and $R^2$ is a methyl group and the other of $R^1$ and $R^2$ is a hydrogen atom.

In General Formula (1), n is an integer of 2 to 4, preferably an integer of 2 to 3, and more preferably 2.

In General Formula (1), m is an integer of 1 to 20, preferably an integer of 1 to 10, more preferably an integer of 1 to 6, still more preferably an integer of 1 to 4, and particularly preferably an integer of 1 or 2.

In General Formula (1), $L^2$ is a divalent linking group having 1 to 6 carbon atoms. $L^2$ is not particularly limited as long as it is a divalent linking group having 1 to 6 carbon atoms. $L^2$ is preferably a linear, branched or cyclic alkylene group which may have a substituent or an arylene group, and more preferably a linear alkylene group having 2 to 6 carbon atoms.

The substituent of the alkylene group is not particularly limited, but it is preferably a substituent selected from Substituent Group A and more preferably an oxo group.

In General Formula (1), Y is a group represented by the following Formula (3).

(3)

In Formula (3), $R^4$ and $R^5$ are the same or different and are an alkyl group having 1 to 40 carbon atoms. Preferred is an alkyl group having 4 to 32 carbon atoms, more preferred is an alkyl group having 6 to 28 carbon atoms, and still more preferred is an alkyl group having 8 to 24 carbon atoms. Further, $R^4$ and $R^5$ may be linear, branched or cyclic and may have a substituent. Examples of the substituent include Substituent Group A.

$R^4$ and $R^5$ are the same or different and are particularly preferably a group selected from an n-octyl group, a 2-ethylhexyl group, a nonyl group, a decyl group, an undecyl group, a dodecyl group, a tetradecyl group, a hexadecyl group, an octadecyl group, an eicosyl group, a docosyl group, a tetracosyl group, a 9-octadecen-1-yl group and an octadecadien-1-yl group.

Hereinafter, examples of the compound represented by General Formula (1) according to the present invention are shown, but the present invention is not limited thereto.

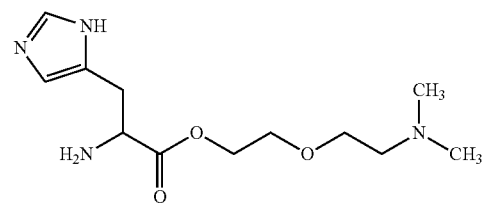

I-1

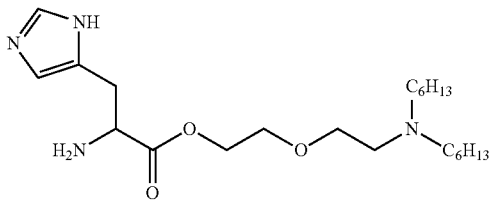

I-2

-continued

-continued

I-17

I-18

I-19

I-20

I-21

I-22

I-23

I-24

I-25

I-26

I-27

I-28

R: —(CH$_2$)$_2$CH=CH(CH$_2$)$_8$CH=CH(CH$_2$)$_3$CH$_3$

I-29

I-30

-continued

I-31, I-32, I-33, I-34, I-35, I-36, I-37, I-38, I-39, I-40, I-41, I-42, I-43, I-44

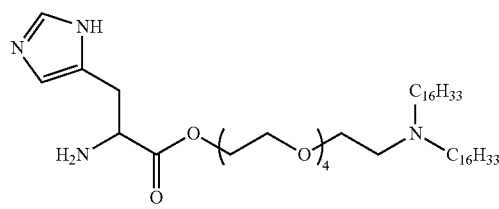
I-45
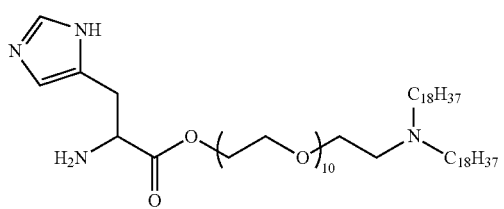
I-52
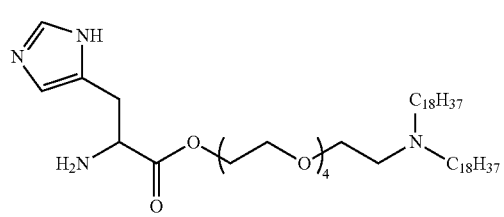
I-46
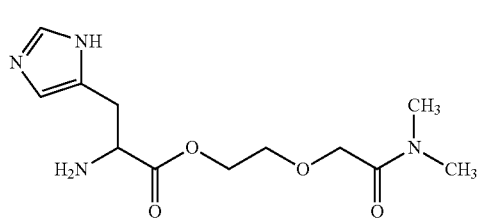
I-53
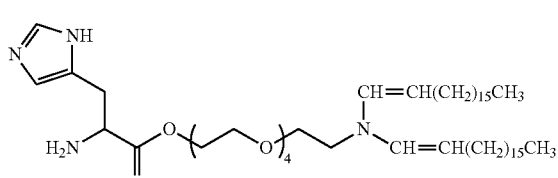
I-47
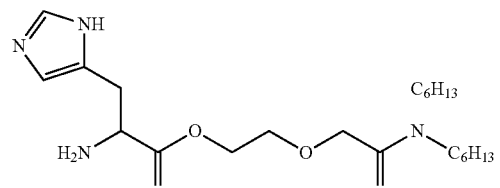
I-54
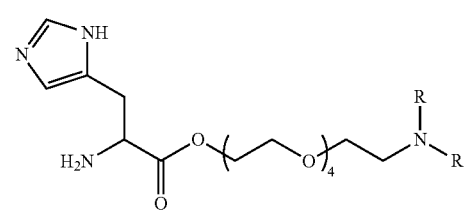
I-48
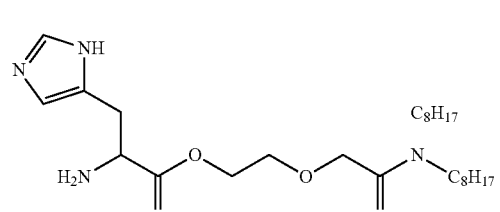
I-55
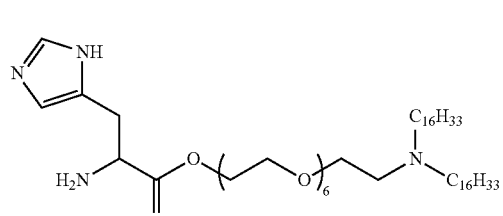
I-49
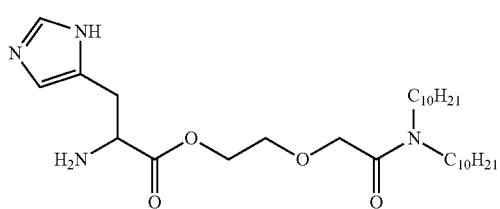
I-56
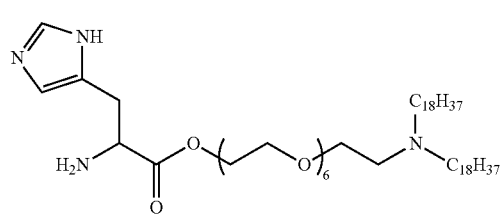
I-50
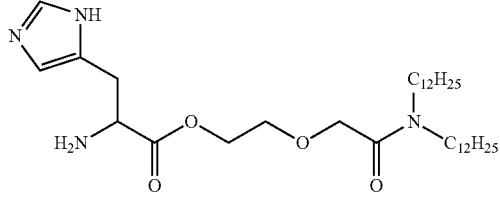
I-57
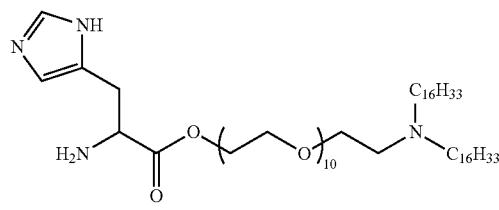
I-51
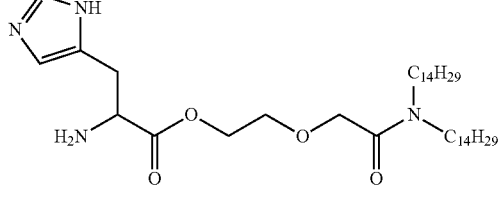
I-58

I-59 — I-72 (chemical structures, no extractable text beyond labels)

I-66 R: —(CH$_2$)$_2$CH=CH(CH$_2$)$_8$CH=CH(CH$_2$)$_3$CH$_3$

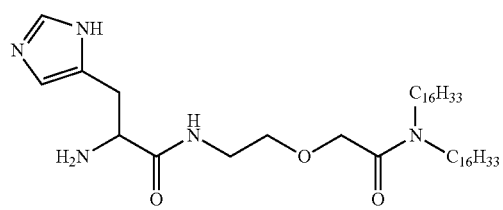
I-73
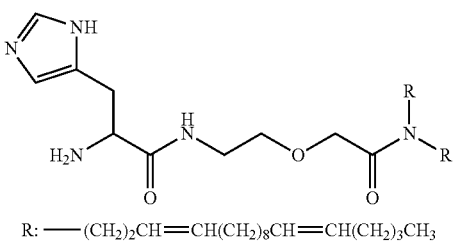
I-80
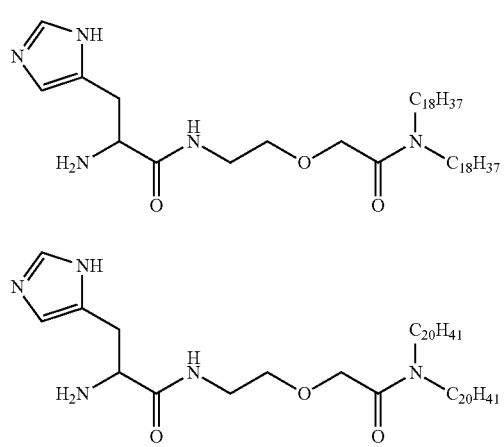
I-74
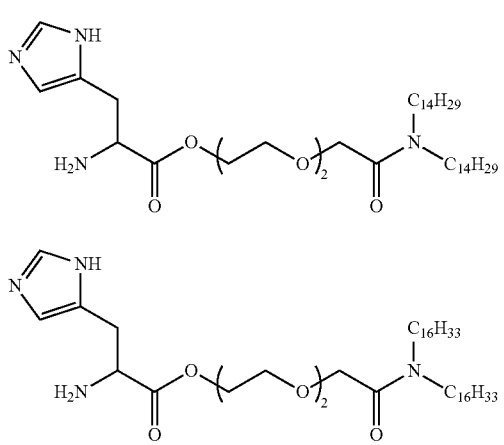
I-81
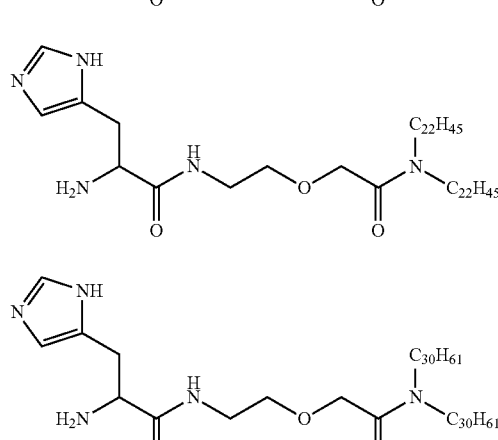
I-75
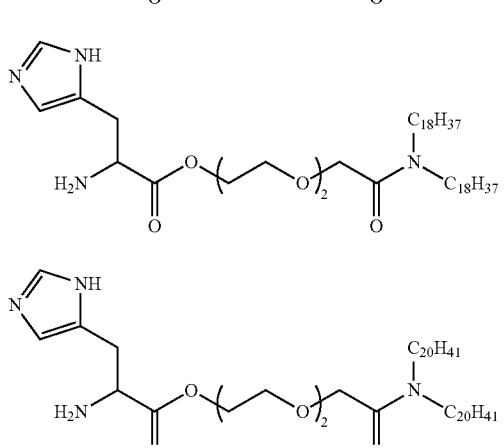
I-82
I-76
I-83
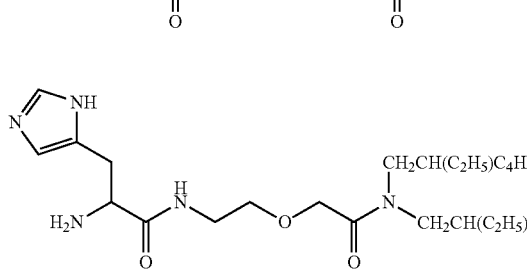
I-77
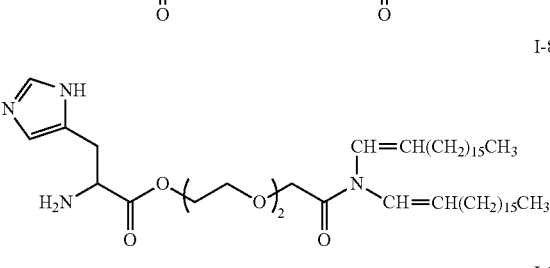
I-84
I-78
I-85
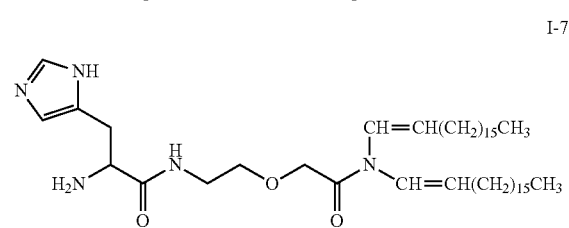
I-79
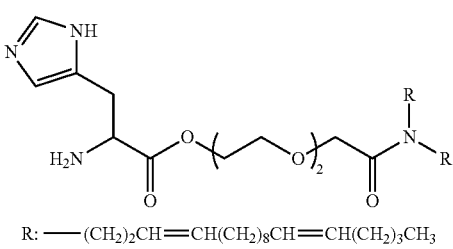
I-86

-continued

I-87, I-88, I-89, I-90, I-91, I-92, I-93, I-94, I-95, I-96, I-97, I-98, I-99, I-100

-continued
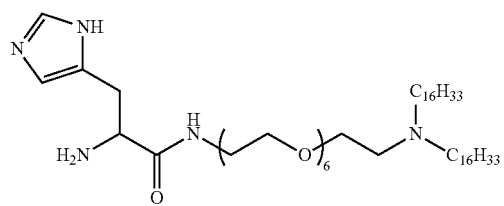
I-101
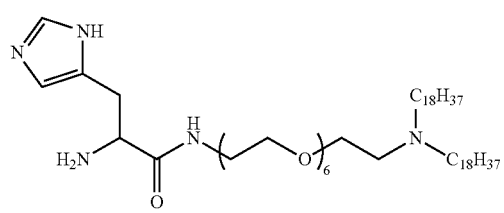
I-102
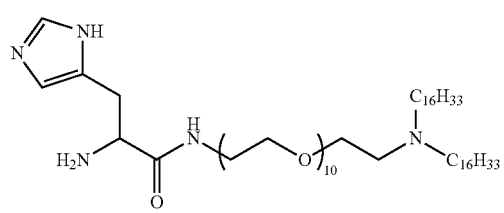
I-103
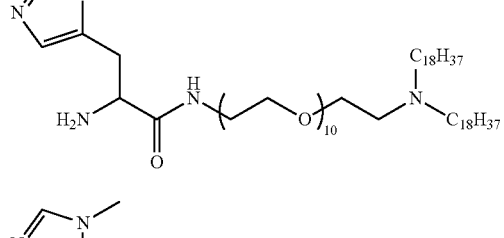
I-104
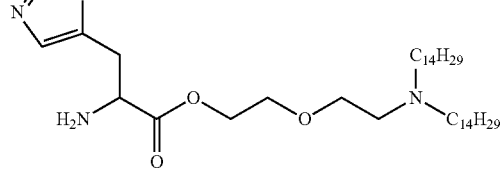
I-105
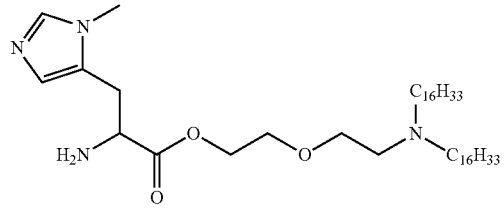
I-106
I-107
-continued
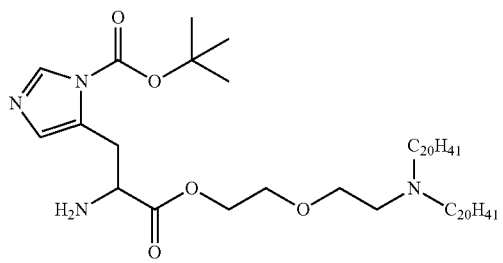
I-108
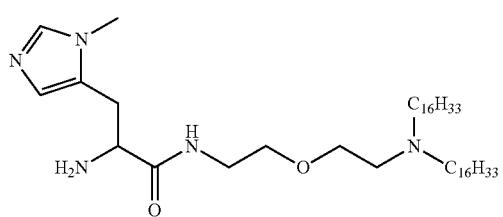
I-109
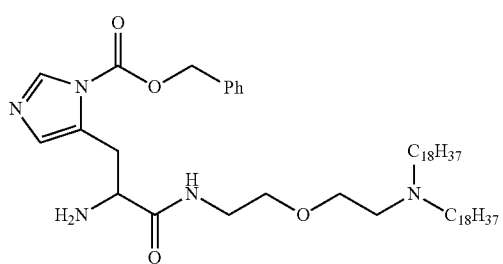
I-110
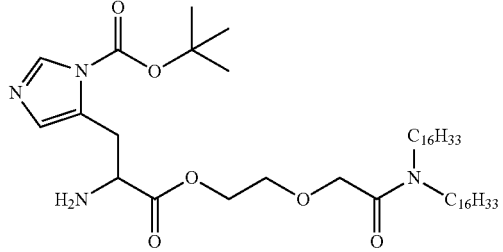
I-111
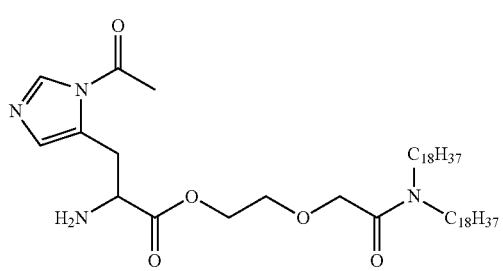
I-112
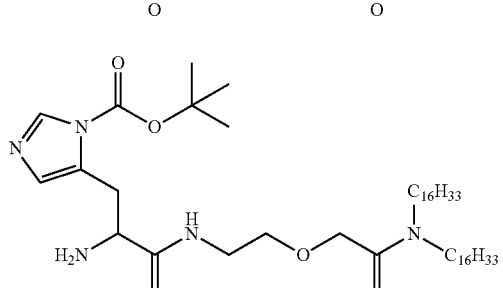
I-113

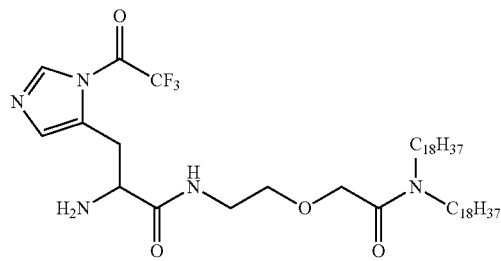
I-114
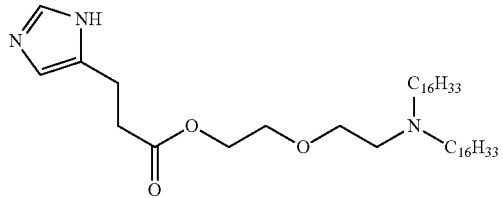
I-120
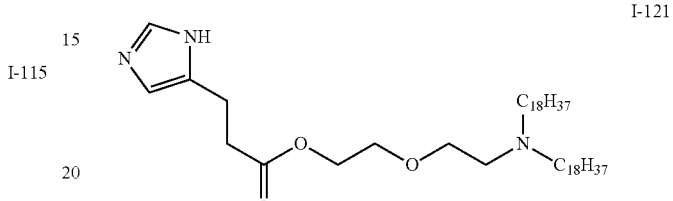
I-115
I-121
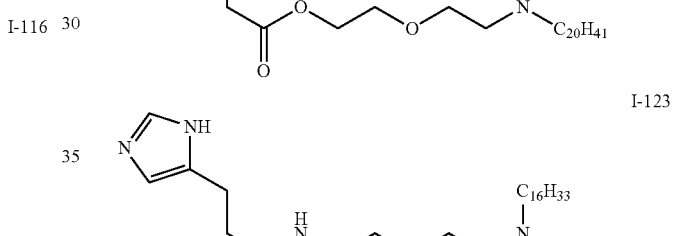
I-116
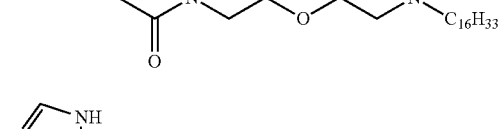
I-122
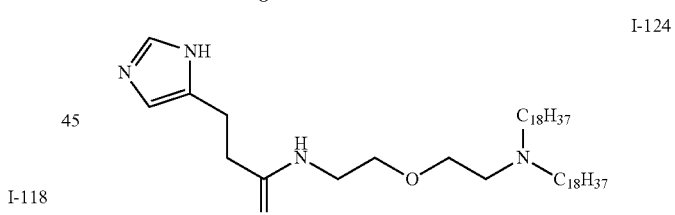
I-117
I-123
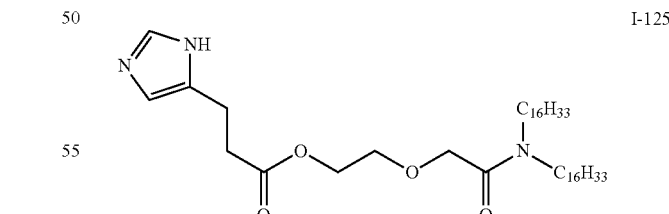
I-118
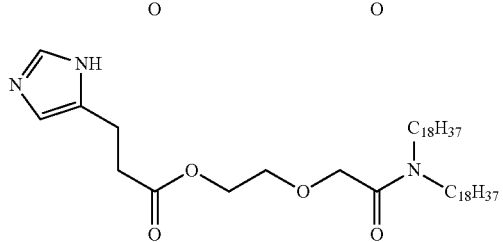
I-119, I-124, I-125, I-126

| | |
|---|---|
| I-127 | I-135 |
| I-128 | I-136 |
| I-129 | I-137 |
| I-130 | I-138 |
| I-131 | I-139 |
| I-132 | I-140 |
| I-133 | I-141 |
| I-134 | I-142 |
| | I-143 |
| | I-144 |
| | I-145 |

-continued
I-146
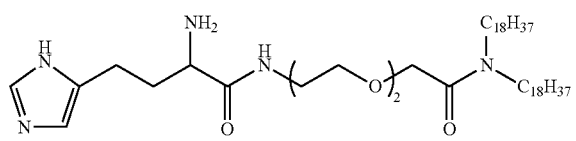
I-147
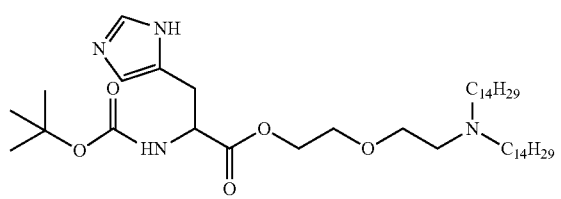
I-148
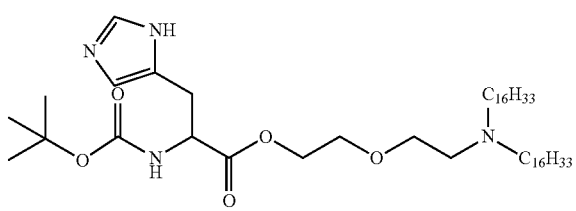
I-149
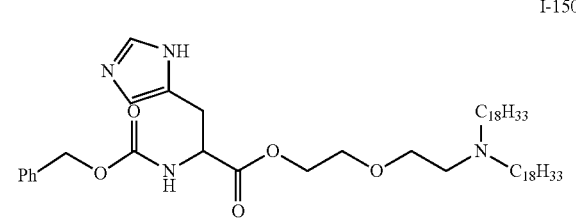
I-150
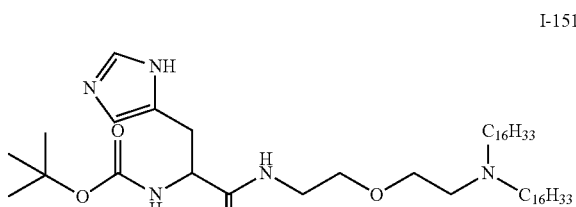
I-151
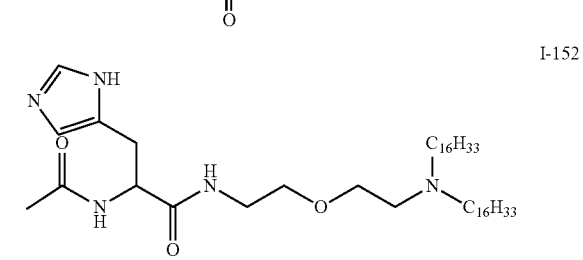
I-152
-continued
I-153
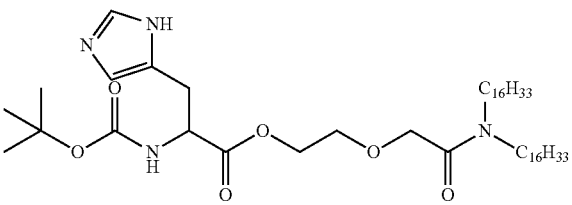
I-154
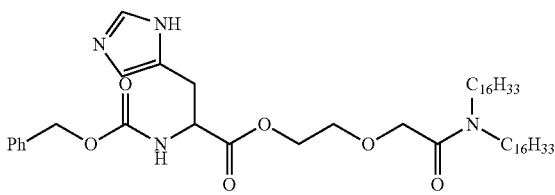
I-155
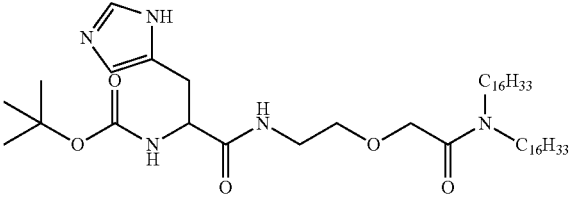
I-156
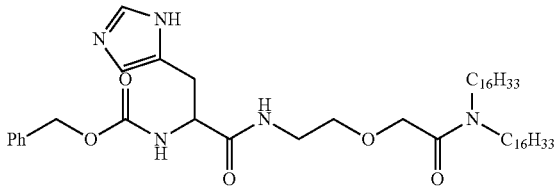
I-157
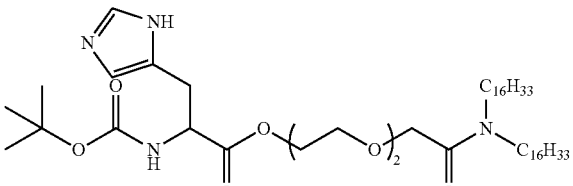
I-158
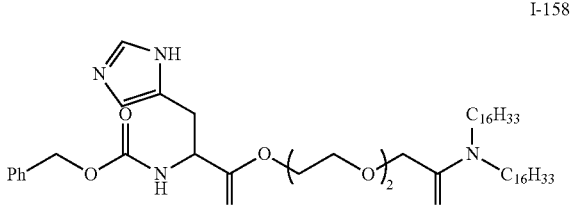
I-159
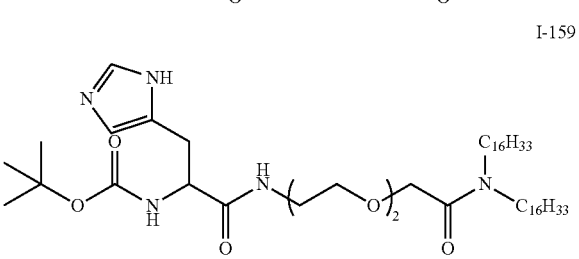

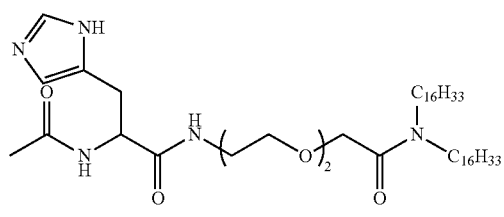
I-160
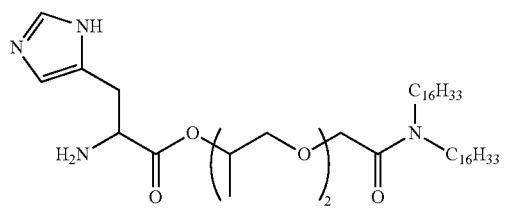
I-167
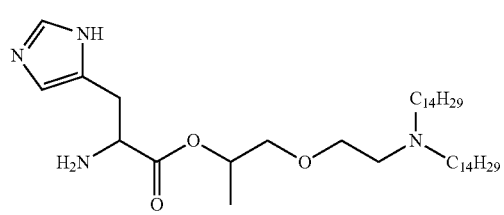
I-161
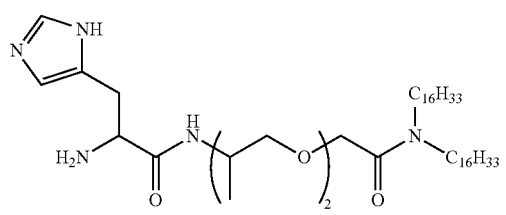
I-168
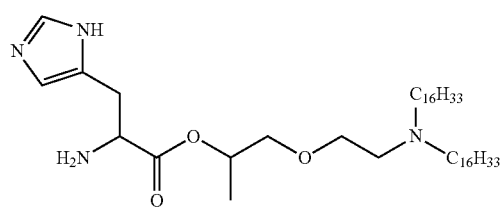
I-162
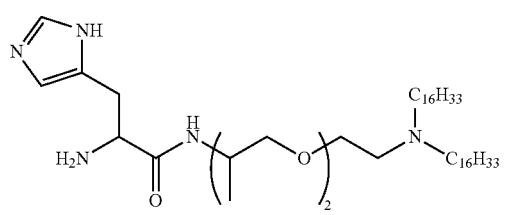
I-169
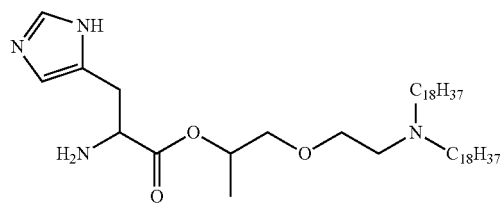
I-163
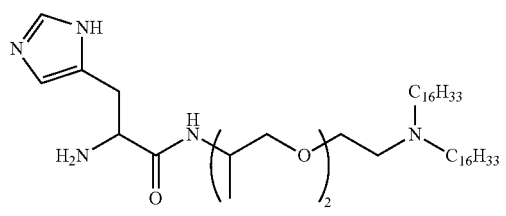
I-170
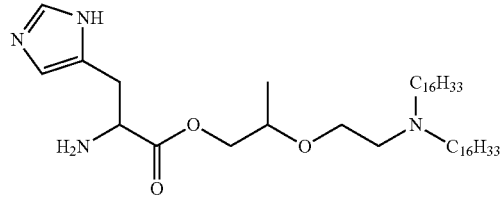
I-164
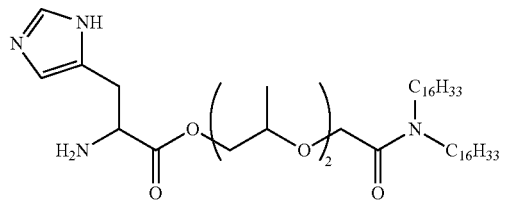
I-171
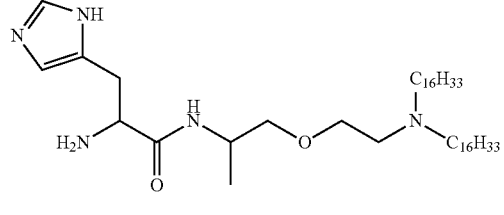
I-165
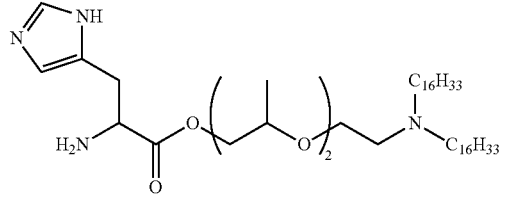
I-172
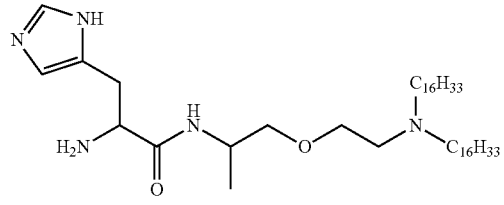
I-166
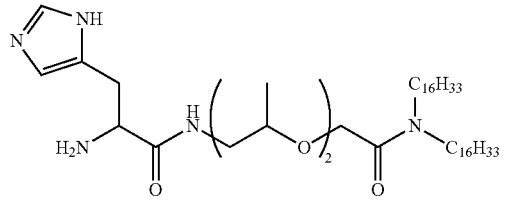
I-173

I-174
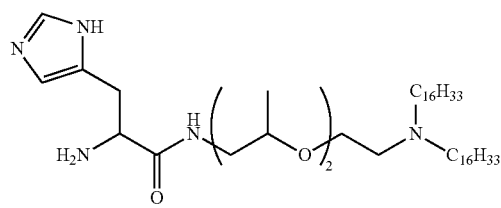
I-175
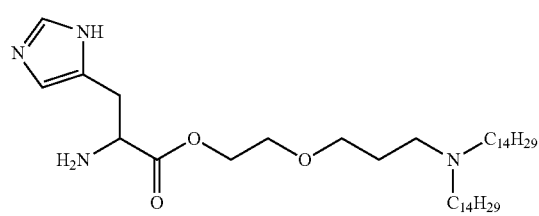
I-176
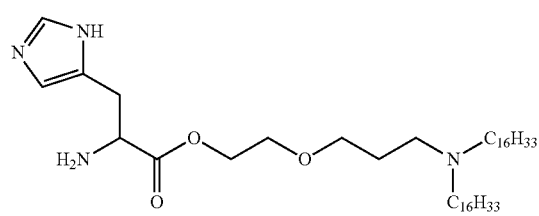
I-177
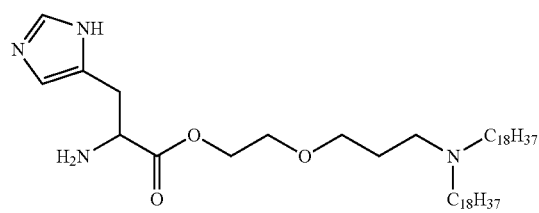
I-178
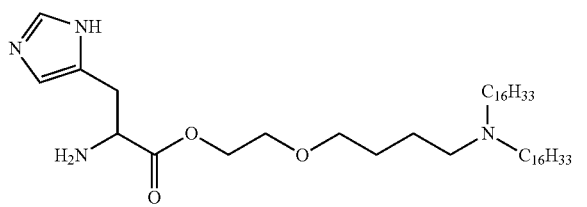
I-179
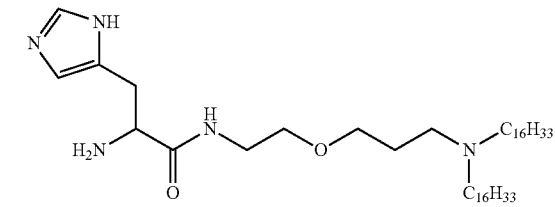
I-180
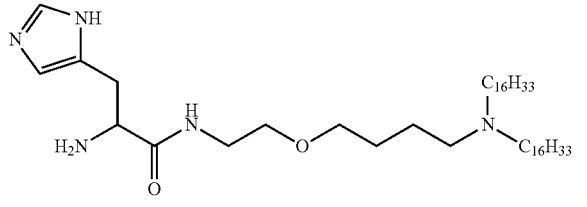
I-181
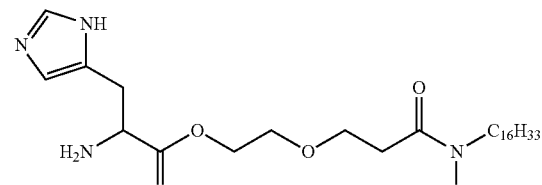
I-182
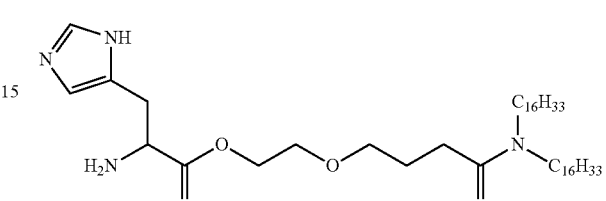
I-183
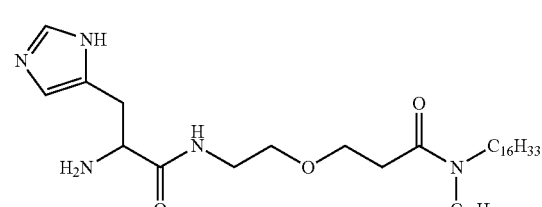
I-184
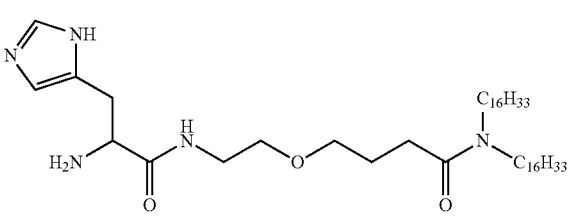
I-185
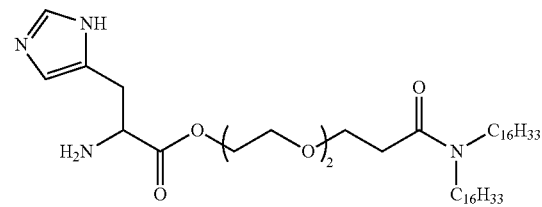
I-186
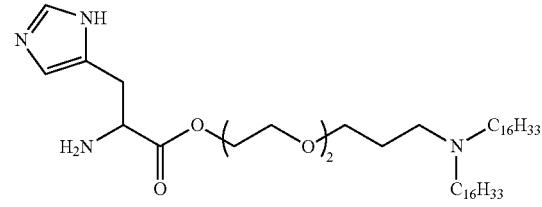
I-187
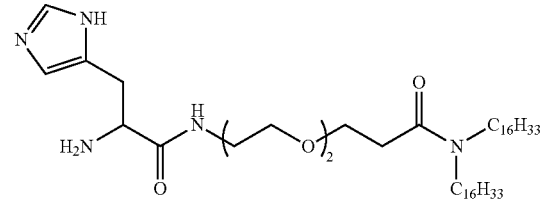

-continued

I-188

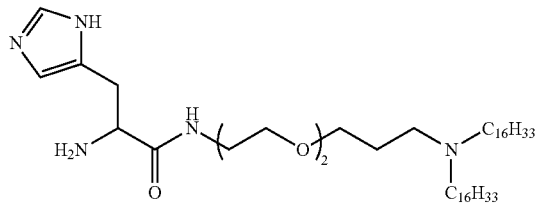

The compound represented by General Formula (1) according to the present invention has a structure containing a specific ether bond as a repeating unit and a terminal structure having a dialkylamino group.

For example, in a case where the compound of the present invention is used as a membrane-constituting lipid of liposomes, a terminal dialkylamino group functions as an effective hydrophobic group. Meanwhile, the structure containing an ether bond as a repeating unit is a structure having high hydrophilicity and is therefore thought to contribute to the improvement of dispersibility during the formation of liposomes. The compound represented by General Formula (1) according to the present invention has a very excellent effect as a membrane-constituting lipid of liposomes as these partial structures function.

In addition, the compound represented by General Formula (1) according to the present invention has an alkylene group represented by $L^1$. Therefore, it is possible to prevent an intramolecular cyclization reaction, so the compound represented by General Formula (1) according to the present invention exhibits excellent stability.

Hereinafter, a method for producing the compound represented by General Formula (1) is shown.

The method for producing the compound represented by General Formula (1) is not particularly limited. For example, the compound represented by General Formula (1) can be produced by combining known peptide synthesis methods. In a case where it is necessary to protect or deprotect an amino group, a hydroxyl group or a carboxyl group in reaction steps, any known protecting group may be used.

The above-mentioned reaction may be carried out in the presence of a solvent if necessary. The type of the solvent to be used is not particularly limited, and examples thereof include water or any organic solvents (tetrahydrofuran, dioxane, diethyl ether, dichloromethane, chloroform, dichloroethane, benzene, toluene, xylene, chlorobenzene, dichlorobenzene, dimethylformamide, dimethylacetamide, acetonitrile, nitromethane, dimethyl sulfoxide, methanol, ethanol, propanol, methyl acetate, ethyl acetate, hexane, heptane, N-methylpyrrolidone, N-ethylpyrrolidone, and the like) and mixtures thereof.

In a case where it is necessary to carry out esterification or amidation, such a reaction may be carried out by any known method selected from a method using an acid catalyst (for example, sulfuric acid, methanesulfonic acid, or p-toluenesulfonic acid), a method using a condensation agent (for example, 1,3-dicyclohexylcarbodiimide, 1-ethyl-3-(3-dimethylaminopropyl)carbodiimide hydrochloride, carbonyldiimidazole, N-hydroxysuccinimide, N-hydroxybenzotriazole, or 3,4-dihydro-3-hydroxy-4-oxo-1,2,3-benzotriazine), an ester exchange method, an ester-amide exchange method, and the like. The reaction of esterification or amidation may be carried out in liquid phase or may be carried out in solid phase synthesis.

In the synthesis of the compound represented by General Formula (1) and its intermediates, separation and purification thereof from the unreacted raw materials, by-products and other impurities may be carried out if necessary. Separation and purification may be carried out by a conventional method which may be selected from any known methods, for example, extraction with an organic solvent, recrystallization, crystallization using a poor solvent, and chromatography using silica gel or molecular sieve.

A liposome containing the imidazole compound represented by General Formula (1), which is another aspect of the present invention, will be described in detail.

The liposome of the present invention is a composition including liposomes containing the compound of the present invention. The liposome of the present invention contains at least a lipid constituting the liposome, in addition to the compound of the present invention. For example, the liposome of the present invention, together with the compound of the present invention, a lipid constituting the liposome and a substance to be introduced into cells or the like (for example, nucleic acid), can be used as a composition for introducing a substance into cells or the like.

In the liposome of the present invention, the content of the compound of the present invention may be suitably determined depending on the type of the substance to be introduced, applications, the form of the composition or the like, but it is preferably set to 0.5 to 50 mol % and more preferably 1 to 10 mol %, with respect to the total lipid amount.

Examples of the lipids used in the liposome of the present invention include phospholipids such as phosphatidylethanolamines, phosphatidylcholines, phosphatidylserines, phosphatidylinositols, phosphatidylglycerols, cardiolipins, sphingomyelins, plasmalogens, and phosphatidic acid, and sterols such as cholesterol and cholestanol. These lipids may be used alone or in combination of two or more thereof. Among these, it is preferable to use a combination of phospholipids and sterols. The fatty acid residue in the phospholipid is not particularly limited, and examples thereof include saturated or unsaturated fatty acid residues having 12 to 18 carbon atoms. Preferred are a myristoyl group, a palmitoyl group, a stearoyl group, an oleoyl group, and a linoleyl group.

Regarding the amount of lipids in the liposome of the present invention, phospholipids including compound of the present invention are preferably set to 50 to 100 mol % and more preferably 60 to 100 mol %, with respect to the total lipid amount. Sterols are preferably 0 to 50 mol % and more preferably 0 to 40 mol %, with respect to the total lipid amount.

The substance applied and introduced into the liposome of the present invention may be any of oligonucleotides, DNAs, RNAs, nucleic acids containing both sugars of deoxyribose and ribose, synthetic artificial nucleic acids, and functional artificial nucleic acids to which PEGs, antibodies, membrane-permeable peptides or lipids or the like are directly bonded. Examples of such a substance include short oligonucleotides such as antisense oligonucleotides, antisense DNAs, antisense RNAs, siRNAs, and miRNAs; physiologically active substances such as enzymes and cytokines; genes encoding antisense RNAs, siRNAs, or miRNAs; and peptide nucleic acids.

The liposome of the present invention is preferably a form dispersed in an aqueous solvent, and may take a form of monolayer or multi-layer or the like. Although the particle size of the liposome in a dispersed state is not limited, an average particle size of the liposome is 5 nm to 5 μm and preferably 150 to 250 nm. Measurement of an average particle size may be carried out using a known method. Although not limited to the following, the average particle size may be measured by 10 to 50-fold diluting a dispersion liquid of liposomes of the present invention with water or a buffer to be used, for example, using a zeta potential-particle size measurement system from Otsuka Electronics Co., Ltd.

A method for producing the liposome of the present invention will be described. Although the production method is not limited, the liposome of the present invention can be produced by dissolving all or part of the components of the liposome in an organic solvent or the like, and performing dryness under reduced pressure using an evaporator or spray-drying using a spray dryer. Then, where appropriate, in a case where it is desired to disperse in an aqueous solvent, the liposome can be produced by adding the above dried mixture to the aqueous solvent, followed by emulsification using emulsification equipment such as a homogenizer, an ultrasonic emulsifier, a high-pressure injection emulsifier, or the like.

The composition of the aqueous solvent (dispersion medium) in the liposome of the present invention is not limited, and examples thereof include a buffer such as phosphate buffer, citrate buffer or phosphate buffered saline, physiological saline, and media for cell culture.

EXAMPLES

The present invention will be specifically described with reference to the following Examples, but the scope of the present invention is not limited thereto.

Example 1

Synthesis of Compound I-7

According to the following synthetic scheme, Compound I-7 was synthesized.

at an internal temperature of 80° C. for 4 hours and 40 minutes. The reaction system was returned to room temperature, ethyl acetate was added thereto, and the organic layer was successively washed with water and saturated saline in a separating funnel. The organic layer was dried over anhydrous magnesium sulfate, and the solvent was distilled off, followed by purification by silica gel column chromatography to give 34.2 g (yield of 65%) of Intermediate 1. In $^1$H-NMR data, it was identified as Intermediate 1 since peaks of individual protons were observed at the characteristic positions.

(Synthesis of Intermediate 2)

5.36 g (10.0 mmol) of N-α,N-τ-di(t-butoxycarbonyl)-L-histidine·dicyclohexylammonium salt and 50 mL of dichloromethane were taken in a reaction container, and an internal temperature of the reaction container was set to 0° C. 2.30 g (12.0 mmol) of 1-ethyl-3-(3-dimethylaminopropyl)carbodiimide hydrochloride was added thereto, followed by stirring at 0° C. for 1 hour. 5.54 g (10.0 mmol) of Intermediate 1 and 122 mg (1 mmol) of 4-dimethylaminopyridine were added thereto, and the mixture was stirred at 0° C. for 30 minutes and then allowed to react at 25° C. for 12 hours. The solvent was distilled off, followed by purification by silica gel column chromatography to give 7.0 g (yield of 78%) of Intermediate 2. In $^1$H-NMR data, it was identified as Intermediate 2 since peaks of individual protons were observed at the characteristic positions.

(Synthesis of Compound I-7)

4.95 g (5.6 mmol) of Intermediate 2 and 5 mL of dichloromethane were taken in a reaction container, and the mixture was stirred at an internal temperature of 0° C. to prepare a homogeneous solution. 5.0 g (44.5 mmol) of trifluoroacetic acid was added thereto, followed by stirring at an internal temperature of 0° C. for 30 minutes, and 2.5 g (22.3 mmol) of trifluoroacetic acid was added thereto, followed by stirring at room temperature for 3 hours. The

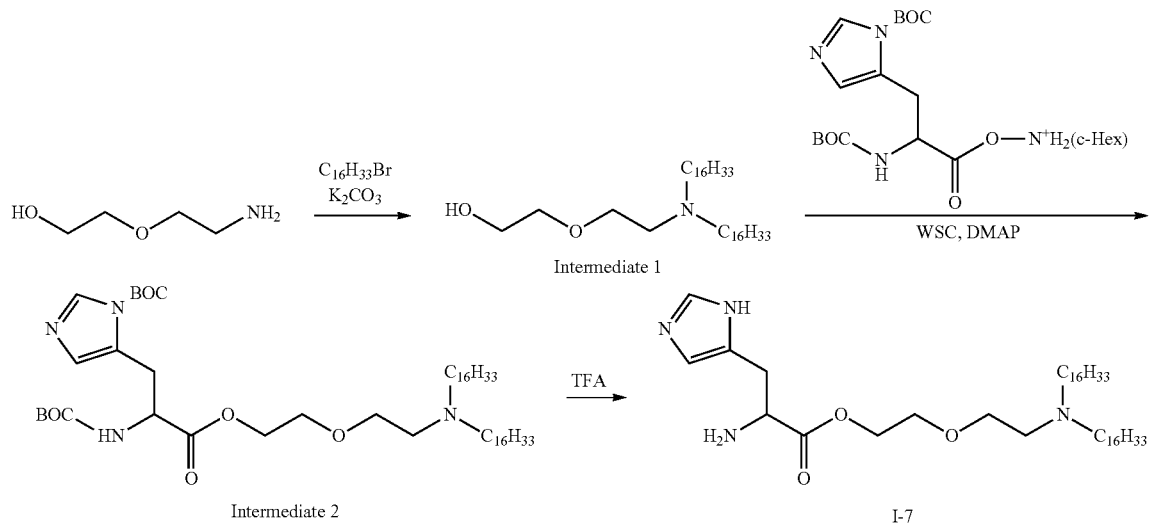

(Synthesis of Intermediate 1)

10.0 g (95.1 mmol) of 2-aminoethoxyethanol, 58.1 g (190.2 mmol) of 1-bromohexadecane, 100 mL of dimethyl sulfoxide, and 52.6 g (380.4 mmol) of potassium carbonate were taken in a reaction container, followed by heating at an internal temperature of 60° C. for 2 hours, and then heating reaction mixture was neutralized with a saturated aqueous sodium hydrogen carbonate solution, and the organic layer was extracted with ethyl acetate and dried over anhydrous sodium sulfate. The organic layer was concentrated under reduced pressure and purified by silica gel column chromatography to give 1.87 g (yield of 49%) of Compound I-7. In ¹H-NMR data, it was identified as Compound I-7 since peaks of individual protons were observed at the characteristic positions.

Example 2

Synthesis of Compound I-88

According to the following synthetic scheme, Compound I-88 was synthesized.

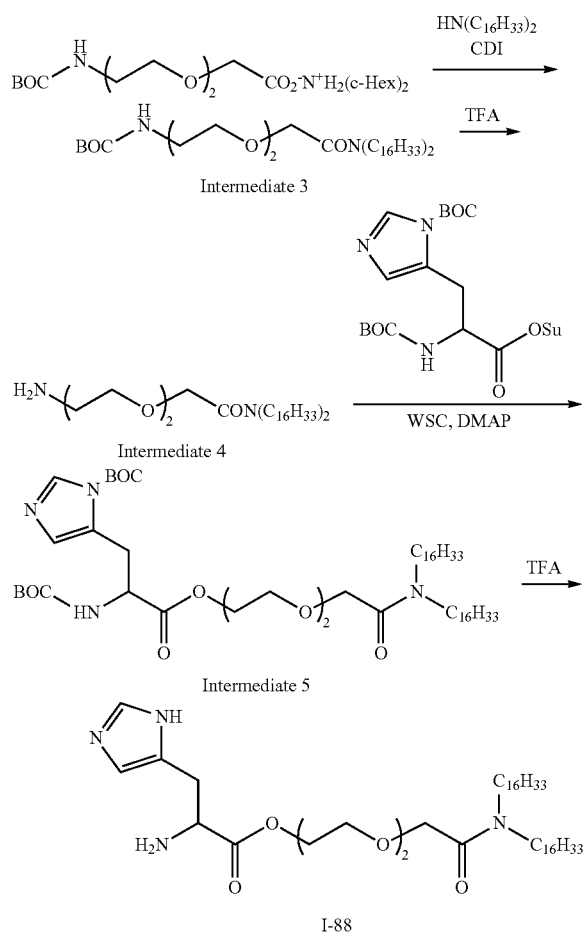

Intermediate 3

Intermediate 4

Intermediate 5

I-88

(Synthesis of Intermediate 3)

2.0 g (4.5 mmol) of 8-(t-butoxycarbonyl)amino-3,6-dioxaoctanoic acid ·dicyclohexylammonium salt and 20 mL of tetrahydrofuran were taken in a reaction container, and an internal temperature of the reaction container was set to 0° C. 729.4 mg (4.95 mmol) of carbonyldiimidazole was added thereto, followed by stirring at an internal temperature of 0° C. for 30 minutes and then at an internal temperature of 25° C. for 30 minutes. 2.31 g (4.95 mmol) of dihexadecylamine was added thereto, followed by stirring at room temperature for 12 hours and then at 50° C. for 7 hours.

Ethyl acetate was added to the reaction mixture which was then successively washed with water and saturated saline, the organic layer was dried over anhydrous sodium sulfate, and the solvent was distilled off under reduced pressure. The resulting crude product was purified by silica gel column chromatography to give 1.77 g (yield of 55%) of Intermediate 3. In ¹H-NMR data, it was identified as Intermediate 3 since peaks of individual protons were observed at the characteristic positions.

(Synthesis of Intermediate 4)

1.77 g (1.49 mmol) of Intermediate 3 and 20 mL of dichloromethane were taken in a reaction container, and the mixture was stirred at an internal temperature of 0° C. to prepare a homogeneous solution. 2.8 g (25 mmol) of trifluoroacetic acid was added thereto, followed by stirring at an internal temperature of 0° C. for 1 hour and then at room temperature for 12 hours. The reaction mixture was neutralized with a saturated aqueous sodium hydrogen carbonate solution, and the organic layer was extracted with ethyl acetate and dried over anhydrous sodium sulfate. The organic layer was concentrated under reduced pressure and purified by silica gel column chromatography to give 993 mg (yield of 65%) of Intermediate 4. In ¹H-NMR data, it was identified as Intermediate 4 since peaks of individual protons were observed at the characteristic positions.

(Synthesis of Intermediate 5)

993 mg (1.6 mmol) of Intermediate 4, 809 mg (1.8 mmol) of bis(BOC)-L-histidine-N-hydroxysuccinimidyl, and 5 mL of tetrahydrofuran were taken in a reaction container, followed by stirring at 0° C. 181 mg (1.8 mmol) of triethylamine was added thereto, and the temperature of the reaction system was raised to 25° C., followed by stirring for 12 hours. Ethyl acetate was added thereto, the mixture was successively washed with an aqueous citric acid solution and water, and the organic layer was dried over anhydrous sodium sulfate. The organic layer was concentrated under reduced pressure and purified by silica gel column chromatography to give 1.41 g (yield of 91%) of Intermediate 5. In ¹H-NMR data, it was identified as Intermediate 5 since peaks of individual protons were observed at the characteristic positions.

(Synthesis of Compound I-88)

1.41 g (1.48 mmol) of Intermediate 5 and 2 mL of dichloromethane were taken in a reaction container, and dissolved at 0° C. 1.66 g (14.8 mmol) of trifluoroacetic acid was added thereto, followed by stirring at 0° C. for 1 hour and then at 25° C. for 3 hours. The reaction mixture was neutralized with a saturated aqueous sodium hydrogen carbonate solution, and the organic layer was extracted with ethyl acetate and dried over anhydrous sodium sulfate. The organic layer was concentrated under reduced pressure and purified by silica gel column chromatography to give 833 mg (yield of 75%) of Compound I-88. In ¹H-NMR data, it was identified as Compound I-88 since peaks of individual protons were observed at the characteristic positions.

Example 3

Synthesis of Compound I-90

According to the following synthetic scheme, Compound I-90 was synthesized.

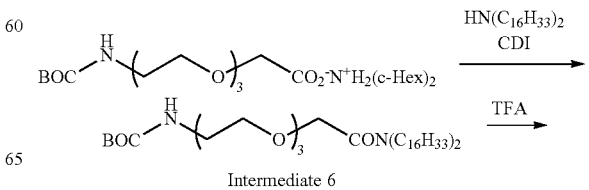

Intermediate 6

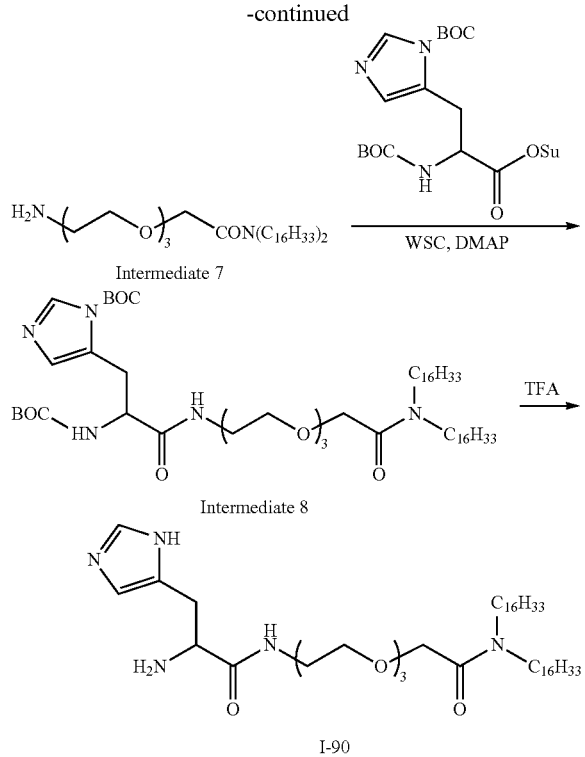

(Synthesis of Intermediate 6)

1.1 g (2.33 mmol) of 11-(t-butoxycarbonyl)amino-3,6,9-trioxaundecanoic acid-dicyclohexylammonium salt and 20 mL of tetrahydrofuran were taken in a reaction container, and an internal temperature of the reaction container was set to 0° C. 416.1 mg (2.56 mmol) of carbonyldiimidazole was added thereto, followed by stirring at an internal temperature of 0° C. for 30 minutes and then at an internal temperature of 25° C. for 30 minutes. 1.09 g (2.33 mmol) of dihexadecylamine was added thereto, followed by stirring at room temperature for 2 hours and then 40° C. for 6 hours.

Ethyl acetate was added to the reaction mixture which was then successively washed with water and saturated saline, the organic layer was dried over anhydrous sodium sulfate, and the solvent was distilled off under reduced pressure. The resulting crude product was purified by silica gel column chromatography to give 1.04 g (yield of 59%) of Intermediate 6. In $^1$H-NMR data, it was identified as Intermediate 6 since peaks of individual protons were observed at the characteristic positions.

(Synthesis of Intermediate 7)

1.04 g (1.38 mmol) of Intermediate 6 and 3 mL of dichloromethane were taken in a reaction container, followed by stirring at an internal temperature of 0° C. to prepare a homogeneous solution. 1.5 g (13.8 mmol) of trifluoroacetic acid was added thereto, followed by stirring at an internal temperature of 0° C. for 1 hour and then stirring at room temperature for 12 hours. The reaction mixture was neutralized with a saturated aqueous sodium hydrogen carbonate solution, and the organic layer was extracted with ethyl acetate and dried over anhydrous sodium sulfate. The organic layer was concentrated under reduced pressure and purified by silica gel column chromatography to give 789 mg (yield of 87%) of Intermediate 7. In $^1$H-NMR data, it was identified as Intermediate 7 since peaks of individual protons were observed at the characteristic positions.

(Synthesis of Intermediate 8)

789 mg (1.2 mmol) of Intermediate 7, 600 mg (1.3 mmol) of bis(BOC)-L-histidine-N-hydroxysuccinimidyl ester, and 10 mL of tetrahydrofuran were taken in a reaction container, followed by stirring at 0° C. 131 mg (1.3 mmol) of triethylamine was added thereto, and the reaction system was raised to 25° C., followed by stirring for 12 hours. Ethyl acetate was added thereto, the mixture was successively washed with an aqueous citric acid solution and water, and the organic layer was dried over anhydrous sodium sulfate. The organic layer was concentrated under reduced pressure and purified by silica gel column chromatography to give 919 mg (yield of 77%) of Intermediate 8. In $^1$H-NMR data, it was identified as Intermediate 8 since peaks of individual protons were observed at the characteristic positions.

(Synthesis of Compound I-90)

919 mg (0.93 mmol) of Intermediate 8 and 2 mL of dichloromethane were taken in a reaction container and dissolved at 0° C. 2.07 g (18.5 mmol) of trifluoroacetic acid was added thereto, followed by stirring at 0° C. for 1 hour and then at 25° C. for 3 hours. The reaction mixture was neutralized with a saturated aqueous sodium hydrogen carbonate solution, and the organic layer was extracted with ethyl acetate and dried over anhydrous sodium sulfate. The organic layer was concentrated under reduced pressure and purified by silica gel column chromatography to give 306 mg (yield of 42%) of Compound I-90. In $^1$H-NMR data, it was identified as Compound I-90 since peaks of individual protons were observed at the characteristic positions.

Example 4

Preparation of Liposomes Using Compound I-7

Preparation of Oil Phase (Coacervation Method)

31 mg of L-α-dipalmitoylphosphatidylcholine, 38 mg of Compound I-7, 33 mg of cholesterol, and 19 mg of N-(carbonyl-methoxypolyethyleneglycol 2000)-1,2-distearoyl-sn-glycero-3-phosphoethanolamine sodium salt (hereinafter, referred to as DSPE-PEG) were respectively weighed to be a molar ratio of 26/22/44/4, and 0.3 mL of ethanol and 0.7 mL of ethyl acetate were added and dissolved to prepare an oil phase.

Preparation of Nucleic Acid-Bearing Liposomes

To the oil phase obtained in the above-mentioned process were added 0.25 mL of an aqueous nucleic acid solution of 5 mg of siRNA to be described below dissolved in 0.263 mL of sterile water and also 1.0 mL of sterile water, followed by heating at 55° C. for 10 minutes. Thereafter, the reaction solution was allowed to cool at room temperature while stirring. Subsequently, the reaction solution was dialyzed at room temperature using a 100 mM histidine solution, and the mixed solvent of ethanol and ethyl acetate was removed. The resulting liquid was granulated by passing it through a 0.4 μm filter using an extruder (Mini Extruder manufactured by Avanti Polar Lipids, Inc.), thereby obtaining nucleic acid-bearing liposomes.

Example 5

Preparation of Liposomes Using Compound I-88

The oil phase was prepared in the same manner as in Example 4, except that 31 mg of L-α-dipalmitoylphosphatidylcholine, 40 mg of Compound I-88, 33 mg of cholesterol, and 19 mg of DSPE-PEG were respectively weighed to be a molar ratio of 26/22/44/4.

Example 6

Preparation of Liposomes Using Compound I-90

The oil phase was prepared in the same manner as in Example 4, except that 38 mg of L-α-dipalmitoylphosphatidylcholine, 40 mg of Compound I-90, 33 mg of cholesterol, and 19 mg of DSPE-PEG were respectively weighed to be a molar ratio of 26/22/44/4.

Comparative Example 1

Preparation of Liposomes Using Comparative Compound

The oil phase was prepared in the same manner as in Example 4, except that 38 mg of L-α-dipalmitoylphosphatidylcholine, 38 mg of the following Compound C-1 described in WO2006/118327A, 33 mg of cholesterol, and 19 mg of DSPE-PEG were respectively weighed to be a molar ratio of 26/22/44/4.

Compound C-1 described in WO2006/118327A is the following compound.

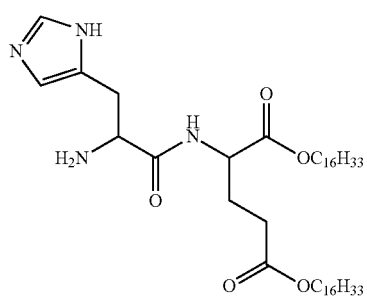

C-1

Compound C-1 was obtained using the synthetic method described in WO2006/118327A.

The following sequences were used as siRNAs.

```
                                              (SEQ ID NO: 1)
5'-GUUCAGACCACUUCAGCUU-3' (sense strand)

(SEQ ID NO: 2)
3'-CAAGUCUGGUGAAGUCGAA-5' (antisense strand)
```

Measurement of Particle Size

The particle size of lipid particles was measured using a zeta potential-particle size measurement system (from Otsuka Electronics Co., Ltd.) by 10 to 50-fold diluting a lipid particle dispersion liquid in water or a buffer to be used.

Table 1 shows the evaluation results of the particle size and zeta potential of the liposomes prepared in Examples 4 to 6 using the compounds of Examples 1 to 3 and the liposomes prepared in Comparative Example 1.

TABLE 1

|  | Particle size (nm) | Zeta potential (mV) |
| --- | --- | --- |
| Example 4 | 170 | 53.6 |
| Example 5 | 209 | 34.5 |
| Example 6 | 199 | 44.0 |
| Comparative Example 1 | Aggregate formed | 50.8 |

The compounds obtained in Example 1, Example 2, and Example 3 were all very stable and were also very useful as a membrane-constituting lipid of liposomes. In addition, the liposomes prepared in Example 4, Example 5, and Example 6 were also very stable and were very useful as a nucleic acid delivery carrier. However, the liposomes prepared in Comparative Example 1 gave aggregates (precipitates) immediately after the formation of liposomes, accordingly the stability of the liposomes was not sufficient.

Evaluation of Residual Ratio of Target mRNA in Cells (1) Transfection of Lipid Particles into Cells With respect to a 24-well plate seeded with $0.9 \times 10^3$ TOV112D cells (human ovarian cancer cell line), the medium was replaced with 200 μL of Opti-MEM (registered trademark) on the following day. Then, 100 μL of each of the liposome dispersion liquids prepared in Examples 4 to 6, which had been diluted with Opti-MEM (registered trademark) to be a 3-fold concentration of the treatment concentration, was added to a 24-well plate (total fluid volume: 300 μL). This was followed by culturing in a 5% $CO_2$ incubator for 24 hours to 48 hours.

(2) Extraction of Total RNA

After culture, total RNA was extracted from cells using an RNeasy Mini Kit (QIAGEN, Inc., registered trademark). After measuring absorbance of the total RNA concentration after extraction, the RNA concentration was diluted with RNase-free water to a 5 ng/μL.

(3) Quantitative PCR Reaction

The reverse transcription reaction and the PCR reaction were carried out using a QUANTIFAST PROBE RTPCR KIT (QIAGEN Inc., registered trademark). Primers/probes for siRNA genes to be used were subjected to quantitative PCR by using a TaqMan Gene expression assay (ABI, registered trademark) and using an Mx3000P (Agilent Technologies Japan, Ltd., registered trademark). PCR conditions were as follows: at 50° C. for 30 minutes; at 95° C. for 15 minutes; at 94° C. for 15 seconds; and at 60° C. for 30 seconds (40 cycles). A TaqMan Encogeneous Control Human ACTB (ABI, registered trademark) was used as an internal standard. The obtained data was calculated in terms of an mRNA residual ratio with relative quantification for non-transfection treatment using a ΔΔCT method.

Table 2 shows the evaluation results of the mRNA residual ratio of the liposomes prepared in Examples 4 to 6.

TABLE 2

|  | siRNA concentration (nM) | mRNA residual ratio (%) |
| --- | --- | --- |
| Example 4 | 10 | 40 |
|  | 30 | 22 |
|  | 100 | 13 |

TABLE 2-continued

| | siRNA concentration (nM) | mRNA residual ratio (%) |
|---|---|---|
| Example 5 | 10 | 81 |
| | 30 | 50 |
| | 100 | 28 |
| Example 6 | 10 | 71 |
| | 30 | 55 |
| | 100 | 38 |

From the above results, it was found that liposome dispersion liquids containing the compound of the present invention and nucleic acid shown in Examples 4 to 6 all exhibit a high inhibitory effect of mRNA production, can stably retain nucleic acid molecules outside cells (in blood), and rapidly release the nucleic acid in the cytoplasm so that original functions of nucleic acid can be efficiently exhibited in target cells. In other words, the liposome containing the compound of the present invention is useful as a nucleic acid carrier.

INDUSTRIAL APPLICABILITY

The compound of the present invention is a novel imidazole compound. Further, the compound of the present invention has high stability and can be used as a membrane-constituting lipid of liposomes. Further, a liposome containing the compound of the present invention is useful as a nucleic acid carrier.

in Formula (1),

Z is an imidazolyl group which may have a substituent, $L^1$ is an alkylene group having 1 to 4 carbon atoms which may have a substituent, and X is an oxygen atom or a group represented by the following Formula (2),

\* is a position of bonding, n is an integer of 2 to 4, m is an integer of 1 to 20, $L^2$ is a divalent linking group having 1 to 6 carbon atoms, and Y is a group represented by the following Formula (3),

$R^1$ and $R^2$ are the same or different and are a hydrogen atom or an alkyl group having 1 to 6 carbon atoms,

What is claimed is:

1. A compound represented by the following General Formula (1):

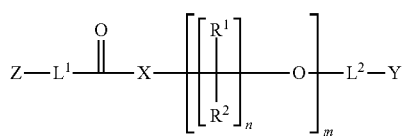

$R^3$ is a hydrogen atom or a substituent, and $R^4$ and $R^5$ are the same or different and are an alkyl group having 1 to 40 carbon atoms.

2. The compound according to claim 1, wherein $L^1$ is an alkylene group represented by the following Formula (4):

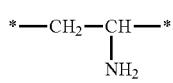

in the formula, \* represents a position of bonding.

3. A liposome comprising the compound according to claim 1.

4. A liposome comprising the compound according to claim 2.

* * * * *